United States Patent [19]
Cousin et al.

[11] Patent Number: 5,464,632
[45] Date of Patent: Nov. 7, 1995

US005464632A

[54] RAPIDLY DISINTEGRATABLE MULTIPARTICULAR TABLET

[75] Inventors: Gérard Cousin, Gallardon; Etienne Bruna, Chartres; Edouard Gendrot, Vernouillet, all of France

[73] Assignee: Laboratoires Prographarm, Chateauneuf, France

[21] Appl. No.: 346,324

[22] Filed: Nov. 29, 1994

Related U.S. Application Data

[63] Continuation of Ser. No. 35,355, Mar. 22, 1993, abandoned.

[30] Foreign Application Priority Data

Jul. 22, 1991 [FR] France .................... 91 09245

[51] Int. Cl.$^6$ ........................................... A61K 9/20
[52] U.S. Cl. .................... 424/465; 424/458; 424/489
[58] Field of Search ................... 424/458, 440, 424/465, 428, 441, 473, 489

[56] References Cited

U.S. PATENT DOCUMENTS

| | | | |
|---|---|---|---|
| 4,915,953 | 4/1990 | Jordan et al. | 424/473 |
| 5,073,374 | 12/1991 | McCarty | 424/465 |
| 5,073,377 | 12/1991 | Alexander et al. | 424/465 |
| 5,215,756 | 6/1993 | Gole et al. | 424/441 |

FOREIGN PATENT DOCUMENTS

| | | |
|---|---|---|
| 0255002 | 7/1987 | European Pat. Off. . |
| 0281200 | 2/1988 | European Pat. Off. . |
| 0408273 | 7/1990 | European Pat. Off. . |

*Primary Examiner*—Thurman K. Page
*Assistant Examiner*—William E. Benston, Jr.
*Attorney, Agent, or Firm*—Caesar, Rivise, Bernstein, Cohen & Pokotilow, Ltd.

[57] ABSTRACT

Rapidly disintegratable multiparticulate tablet the excipient mixture of which is suitable for imparting a disintegration rate such that the tablet disintegrates in the mouth in an extremely short time, notably in less than sixty seconds, characterized by the fact that the active substance is present in the form of coated microcrystals or coated or uncoated microgranules.

6 Claims, No Drawings

5,464,632

1

RAPIDLY DISINTEGRATABLE MULTIPARTICULAR TABLET

This application is a continuation of application Ser. No. 08/035,355, filed Mar. 22, 1993, abandoned.

The invention relates to a rapidly disintegratable multiparticulate tablet, i.e. a pharmaceutical presentation for oral administration whose disintegration rate is such that, when it is placed into the buccal cavity and particularly on the tongue, it disintegrates in less than sixty seconds providing with the saliva present a suspension easy to be swallowed.

The disintegration rate is obtained due to a mixture of excipients or vehicles which comprises generally a disintegrating agent which may consist of a carboxymethylcellulose and a swelling agent which may consist of modified starch.

The active substance or principle is mixed with the abovesaid vehicles, the mixture then being tabletted after addition of a lubricant such as, for example, magnesium stearate.

The Applicants have had the merit of having found that it was possible, unexpectedly and surprisingly, to introduce into a multiparticulate tablet with high disintegration rate such as hereabove defined, the active substance in the form of coated or non-coated microcrystals or microgranules; thus, the physician has at his disposal a rapidly disintegratable multiparticulate tablet proper to facilitate the taking by the patient of most diversified active substances and especially of those whose taste is particularly unpleasant, the said tablet permitting the taking of the said active substances with as diversified features as gastroresistance and controlled release due to the fact that the said coated or non-coated microcrystals and microgranules preserve, after having been shaped in the form of a multiparticulate tablet, their initial properties amongst which masking of taste, gastroresistance and controlled release of the active principle.

Consequently, the rapidly disintegratable multiparticulate tablet according to the invention, which can be used for human beings and for animals, the excipient mixture of which is such as to provide it with a disintegration rate so that its disintegration in the buccal cavity occurs in an extremely short time and especially shorter than sixty seconds, is characterized by the fact that the active substance is in the form of coated or non-coated microcrystals or microgranules with modified action or non-modified action.

According to an advantageous embodiment of the abovesaid tablet, the mixture of excipients comprises one or several disintegrating agents of the carboxymethylcellulose type or insoluble reticulated PVP type, one or several swelling agents which may consist of a carboxymethylcellulose, a starch, a modified starch, for instance a carboxymethylated starch, or a microcrystalline cellulose, and possibly a direct compression sugar consisting for example of 92% of dextrose.

According to an advantageous embodiment, the tablets according to the invention, wherein the active substance is in the form of coated microcrystals, comprise as active substance at least one of those of the group comprising the gastrointestinal sedatives, the antacids, the analgesics, the anti-inflammatory agents, the coronary vasodilators, the peripheral and brain-vasodilators, the anti-infectious agents, the antibiotics, the antiviral agents, the antiparasitic agents, the anticancerous drugs, the antianxiety agents, the neuroleptic drugs, the agents stimulating the central nervous system, the antidepressant drugs, the antihistaminic agents, the antidiarrheal agents, the laxatives, the nutritional supple-

2 ments, the immunodepressant drugs, the cholesterol lowering agents, the hormones, the enzymes, the antispasmodic agents, the antiangorous agents, the drugs acting on the rhythm of the heart, the drugs used in the treatment of arterial hypertension, the anti-migraine agents, the drugs acting on blood coagulability, the antiepileptic agents, the myorelaxing agents, the drugs used in the treatment of diabetes, the drugs used in the treatment of thyroidal dysfunctions, the diuretical agents, the anorexigenic drugs, the antiasthmatic agents, the expectorants, the antitussive agents, the mucoregulators, the decongestants, the hypnotics, the antinauseous agents, the hematopoietical agents, the uricosuric agents, the plant extracts, the contrast mediums.

According to another advantageous embodiment, the tablets according to the invention, wherein the active substance is present in the form of coated or non-coated microgranules with modified action or non-modified action, comprise as active substance at least one of those of the group comprising the gastrointestinal sedatives, the antacids, the analgesics, the anti-inflammatory agents, the coronary vasodilators, the peripheral and brain-vasodilators, the anti-infectious agents, the antibiotics, the antiviral agents, the antiparasitic agents, the anticancerous drugs, the antianxiety agents, the neuroleptic drugs, the agents stimulating the central nervous system, the antidepressant drugs, the antihistaminic agents, the antidiarrheal agents, the laxatives, the nutritional supplements, the immunodepressant drugs, the cholesterol lowering agents, the hormones, the enzymes, the antispasmodic agents, the antiangorous agents, the drugs acting on the rhythm of the heart, the drugs used in the treatment of arterial hypertension, the anti-migraine agents, the drugs acting on blood coagulability, the antiepileptic agents, the myorelaxing agents, the drugs used in the treatment of diabetes, the drugs used in the treatment of thyroidal dysfunctions, the diuretical agents, the anorexigenic drugs, the antiasthmatic agents, the expectorants, the antitussive agents, the mucoregulators, the decongestants, the hypnotics, the antinauseous agents, the hematopoietical agents, the uricosuric agents, the plant extracts, the contrast mediums.

The use of the tablet according to the invention is especially advantageous due to the fact that it may be very easily used by any users. The said tablet can be taken in any condition (when working, when travelling and so on), without a glass and without water. It constitutes an "ambulatory" pharmaceutical presentation which can advantageously be used instead of numerous pharmaceutical presentations such as sachets, effervescent tablets, drinkable ampoules, capsules, traditional tablets and so on.

Its very easy facility of administration is especially interesting when it is necessary that young children or old people take therapeutical substances, i.e. populations which often have swallowing difficulties, i.e. populations which keep the drug in the mouth and which are unable to swallow it. Contrary to the traditional tablet or to the capsule, the tablet according to the invention offers in connection with such populations an advantage of security as, as soon as it is introduced in the mouth, it provides a therapeutical protection.

On the other hand, it is important to emphasize that, even directly swallowed with a little water for example, the said tablet preserves its rapid disintegration rate within the stomach. This type of administration will again raise no security problem.

Furthermore, the tablet according to the invention provides a further big advantage with respect to tablets or simple capsules. In fact until today, people who need to swallow a tablet or a capsule under the above-mentioned conditions (during working, during travelling, without water and without a glass), swallowed the said tablet or capsule without water and that could be dangerous as the tablet or capsule can block in the esophagus and provide thus an important delay as far as absorption of the active principle is concerned or even an ulceration at the level of the esophagus. Similarly, the fact that, on the one hand, the active principle is coated and, on the other hand, that it is present in the form of a multiparticulate tablet, prevents agressive active principles causing ulcerations of the esophagial or gastric mucous membranes, phenomenon which is sometimes caused by certain pharmaceutical presentations which are monolithic, especially when the patient suceeeds in swallowing them with a little water or no water.

Another advantage of the tablet according to the invention is that the said tablet has not the well-known drawbacks of effervescent tablets as for instance the taste which is very unpleasant to the child, the high sodium content which is disturbing to people which must follow a diet without sodium and finally the necessity of having water and a glass for its administration.

Furthermore, it permits the formulation of certain active principles which are not adapted to a previous extracorporeal dissolution and which consequently can be contemplated only under a dry form, which prevents their use in effervescent tablets; consequently, the tablet according to the present invention has all the advantages of the dry forms, i.e. the stability as well as the facility of packaging and storage.

On the other hand, this new pharmaceutical form may contain if necessary two or several active principles which are usually incompatible with one another and this without alteration of their stability.

Another advantage of the tablet according to the invention consists in the possibility of taking by the patient of doses of active principle which are more important than in the past. As a matter of fact as the said tablet is not to be swallowed under its initial form but after disintegration within the buccal cavity, its size might be greater than that of a classical pharmaceutical form which must be adapted to be swallowed without disturbing the taking of the drug.

Finally, the tablet according to the invention has all the advantages of coated particles which permit to obtain especially a taste-masking, a gastroresistance, a delayed release as well as all the advantages of the multiparticulate forms with modified action or non-modified action, i.e. a great exchange surface, the dispersion, less inter- and intra-individual variations, a very reduced gastric empting influence, a very reduced intestinal transit time influence as well as reduced pH influence in the digestive tract, reduced influence of the viscosity and consequently of food and of the position of the body, without local toxic manifestation.

The preparation of the rapidly disintegratable multiparticulate tablets according to the invention is as follows or similar.

When the active principle is in the form of coated microcrystals, it is possible to proceed as follows.

The microcrystals are coated by way of a process known by itself such as, for example, the fluidized air bed, the coacervation and the microencapsulation.

The mixture of excipients is then prepared by the dry- or wet-granulation method.

Then, the coated microcrystals are mixed under dry conditions with the mixture of excipients before compression.

The preparation of the tablet according to the invention wherein the active principle is in the form of coated or non-coated microgranules, may be as follows.

The active principle is put in the form of microgranules by way of a method known by itself such as, for example, extrusion-spheronisation, manufacture in pan, fluidized air bed and so on.

Once obtained, these microgranules are coated if necessary in a pan or in a fluidized air bed.

The mixture of excipients is then prepared by the dry- or wet-granulation method.

Then, the coated or non-coated microgranules are mixed under dry conditions with the mixture of excipients before compression.

The invention may even be better understood by way of the following non-limiting examples which relate to advantageous embodiments of the invention.

EXAMPLE 1

Rapidly disintegratable multiparticulate tablet based on coated crystals of paracetamol.

Tablets according to the invention are prepared whose composition is as follows.

| Formula: | |
|---|---|
| coated paracetamol (with 6% ethylcellulose) | 530 mg |
| direct compression sugar | 160 mg |
| microcrystalline cellulose | 90 mg |
| reticulated polyvinylpyrrolidone | 60 mg |
| sodic carboxymethylcellulose | 50 mg |
| colloidal silica | 6 mg |
| lubricant | 4 mg |
| sweetener | 25 mg |
| aroma | 15 mg |
| magnesium trisilicate | 50 mg |
| Total | 990 mg |

The said tablet is prepared as follows.

The paracetamol crystals are introduced in a fluidized air bed installation and a solution of ethylcellulose in an ethanol/acetone mixture is sprayed thereon.

The excipients are sieved and the coated paracetamol is homogeneized with the excipients inside a mixing device under dry conditions.

Distribution and tabletting are carried out on a compressing machine fitted with punches having a diameter equal to 15 mm and a radius of curvature equal to 20 mm.

The pressure is equal to 16 KNewtons ±1. The hardness of the thus obtained tablets is equal to 100 Newtons ±10. The time of disintegration in the mouth is from 35 to 45 seconds.

EXAMPLE 2

Rapidly disintegratable multiparticulate tablet based on coated cimetidine crystals.

Tablets according to the invention are prepared whose composition is as follows.

| Formula: | |
| --- | --- |
| coated cimetidine (with 15.25% of Eudragit E) | 944 mg |
| reticulated polyvinylpyrrolidone | 89 mg |
| magnesium stearate | 5 mg |
| sweetener | 50 mg |
| aroma | 12 mg |
| Total | 1100 mg |

The said tablet is prepared as follows.

The cimetidine crystals are introduced in a fluidized air bed installation and a solution of a copolymer of dimethyl-aminoethyl-methacrylate and of neutral esters of methacrylic acid known under the trademark "Eudragit E" in alcohol is sprayed thereon.

The excipients are sieved and the coated cimetidine is homogeneized with the excipients inside a mixing apparatus under dry conditions.

Distribution and tabletting are executed on a compressing machine equipped with punches having a diameter equal to 16 mm and a radius of curvature equal to 20 mm.

The pressure is 20 KNewtons ±1. The hardness of the thus obtained tablets is 95 Newtons ±10. The time of disintegration in the mouth is from 15 to 20 seconds.

EXAMPLE 3

Rapidly disintegratable multiparticulate tablet based on coated crystals of paracetamol.

Tablets according to the invention composed as follows are prepared.

| Formula: | |
| --- | --- |
| complex of paracetamol-codeine (30 mg of codeine and 18.4% of Eudragit*) | 627.5 mg |
| reticulated polyvinylpyrrolidone | 90 mg |
| sodium carboxymethylcellulose | 70 mg |
| starch commercialized under the trademark "STARCH 1500" | 100 mg |
| sweetener | 40 mg |
| aroma | 22.5 mg |
| Total | 950 mg |

*Eudragit is a copolymer of methacrylic acid.

This tablet is prepared as follows.

The crystals of paracetamol are introduced in a fluidized air bed installation and the codeine dissolved in a solution of Eudragit E and Eudragit NE 30D (neutral polymer of esters of polymethacrylic acid) is sprayed thereon.

The excipients are sieved and the coated paracetamol is homogeneized with the excipients in a mixing apparatus under dry conditions.

Distribution and tabletting are carried out on a compressing machine equipped with punches having a diameter equal to 16 mm and a radius of curvature equal to 20 mm.

The pressure is 21 KNewtons ±1. The hardness of the thus obtained tablets is 35 Newtons ±5. The time of disintegration in the mouth is from 50 to 60 seconds.

EXAMPLE 4

Rapidly disintegratable multiparticulate tablet based on coated crystals of ibuprofen.

Tablets according to the invention and whose composition is as follows are prepared.

| Formula: | |
| --- | --- |
| ibuprofen (with 10% of ethylcellulose) | 440 mg |
| reticulated polyvinylpyrrolidone | 120 mg |
| starch commercialized under the trademark "STARCH 1500" | 235 mg |
| sweetener | 48 mg |
| aroma | 52 mg |
| magnesium stearate | 5 mg |
| Total | 900 mg |

This tablet is prepared as follows.

The crystals of ibuprofen are introduced in a fluidized air bed installation and a solution of ethylcellulose in ethanol is sprayed thereon.

The excipients are sieved and the coated ibuprofen is homogeneized with the excipients in a mixing apparatus under dry conditions.

Distribution and tabletting are carried out on a compressing machine equipped with punches having a diameter equal to 16 mm and a radius of curvature equal to 20 mm.

The pressure is 15 KNewtons ±1. The hardness of the thus obtained tablets is 50 Newtons ±5. The time of disintegration in the mouth is from 15 to 20 seconds.

EXAMPLE 5

Rapidly disintegratable multiparticulate tablet based on microgranules.

| Formula: | |
| --- | --- |
| microgranules with delayed release based on doxycycline monohydrate (with 100 mg of active principle) | 225 mg |
| microcrystalline cellulose | 142 mg |
| starch commercialized under the trademark "SEPPISTAB ST 500" | 98 mg |
| aspartam | 20 mg |
| aroma | 15 mg |
| Total | 500 mg |

The microgranules are prepared in a pan by coating a neutral sugar sphere with doxycycline according to the classical technology, the microgranules being then coated with Eudragit E also in coating pan.

The tablet is prepared by sieving of the excipients, followed by homogeneization of the microgranules of doxycycline with the excipients in a mixing apparatus under dry conditions, followed by distribution and tabletting in a rotary compressing machine equipped with punches having a diameter equal to 12 mm and radius of curvature is equal to 11 mm.

The pressure is 20 KNewtons ±1. The hardness of the thus obtained tablets is 100 Newtons ±10. The time of disintegration in the mouth is from 10 to 20 seconds.

As a result of which we have a rapidly disintegratable multiparticulate tablet, the constitution and method of manufacture of which are sufficiently disclosed above, such that it would be useless to repeat this subject and about which it is recalled that

- it consists of a tablet which combines a high level technology (control of release, of gastroresistance, of taste-masking of the active principle) with a high security of use due to its multiparticulate form by way of the coating during the process of manufacture and to the fact that its disintegration occurs in the mouth,
- it constitutes an ambulatory form which can be adapted to a great number of active principles and to high dosages, which did not previously exist,
- it offers a high facility of use, as the same pharmaceutical form can be disintegrated within the mouth, in a glass of water or in liquid or semi-liquid food, as for example, in yoghourt for children or infants, or in food for animals in connection with its use in the veterinary field,
- it consists of a single and same pharmaceutical form which can be prescribed to people requiring different strengths; thus, it can be used in connection with an active principle given at its maximum dose and manufactured in a divisible shape at one or several scored places in such a manner that it can be administered in totality or according to the age or the symptoms of the patient, in the form of a divisible part depending upon the shape of the punch, it being emphasized that it was not obvious to obtain a divisible multiparticulate tablet,
- it consequently consists of a pharmaceutical form which is suitable to everybody because it offers a great variety of means for administration and of dosages, which represents a definite economical advantage.

The fact that a single product permits, on the one hand, ways of administration normally permitted by several pharmaceutical forms and that, on the other hand, it gives rise to several posologies normally obtained by the creation of various strengths (tablets or capsules of different concentrations for example) constitutes an economical advantage of primary importance.

In fact from the industrial point of view, this means a single line production instead of several lines production each corresponding to each strength selected and to each pharmaceutical form selected.

We claim:

1. A rapidly disintegratable tablet for oral administration with or without the use of water, said tablet comprising an active substance and a mixture of excipients, wherein said active substance is multiparticulate and in the form of coated microcrystals, coated microgranules or uncoated microgranules and wherein said mixture of excipients comprises excipients which are responsible for the disintegration, said tablet being intended to be swallowed said disintegration occurring in less than sixty seconds under the action of the excipients which are responsible for the disintegration and which are selected from the group consisting at least one disintegrating agent and at least one swelling agent.

2. The tablet of claim 1, wherein the active substance is in the form of coated microcrystals and is selected from the group consisting of gastrointestinal sedatives, antacids, analgesics, anti-inflammatory agents, coronary vasodilators, peripheral and brain-vasodilators, anti-infectious agents, antibiotics, antiviral agents, antiparasitic agents, anticancerous drugs, antianxiety agents, neuroleptic drugs, agents stimulating the central nervous systems, antidepressant drugs, antihistaminic agents, antidiarrheal agents, laxatives, nutritional supplements, immunodepressant drugs, cholesterol lowering agents, hormones, enzymes, antispasmodic agents, antiangorous agents, drugs acting on the rhythm of the heart, drugs used in the treatment of arterial hypertension, anti-migraine agents, drugs acting on blood coagulability, anti-epileptic agents, myorelaxing agents, drugs used in the treatment diabetes, drugs used in the treatment of thyroidal dysfunctions, diuretical agents, anorexigenic drugs, anti-asthmatic agents, expectorants, antitussive agents, mucoregulators, decongestants, hypnotics, antinausea agents, hematopoietical agents, uricosuric agents, plant extracts and contrast mediums.

3. The tablet of claim 1, wherein the active substance is in the form of coated microgranules and is selected from the group consisting of gastrointestinal sedatives, antacids, analgesics, anti-inflammatory agents, coronary vasodilators, peripheral and brain-vasodilators, anti-infectious agents, antibiotics, antiviral agents, antiparasitic agents, anticancerous drugs, antianxiety agents, neuroleptic drugs, agents stimulating the central nervous system, anti-depressant drugs, antihistaminic agents, antidiarrheal agents, laxatives, nutritional supplements, immunodepressant drugs, cholesterol lowering agents, hormones, enzymes, anti-spasmodic agents, antiangorous agents, drugs acting on the rhythm of the heart, drugs used in the treatment of arterial hypertension, anti-migraine agents, drugs acting on blood coagulability, anti-epileptic agents, myorelaxing agents, drugs used in the treatment of diabetes, drugs used in the treatment of thyroidal dysfunctions, diuretical agents, anorexigenic drugs, anti-asthmatic agents, expectorants, antitussive agents, mucoregulators, decongestants, hypnotics, antinausea agents, hematopoietical agents, uricosuric agents, plant extracts and contrast mediums.

4. The tablet of claim 1, wherein the mixture of excipients comprises at least one disintegrating agent selected from the group consisting of carboxymethylcellulose, insoluble reticulated PVP type and at lest one swelling agent selected from the group consisting of starch, modified starch and microcrystalline cellulose.

5. The tablet of claim 1, wherein the mixture of excipients comprises at least one disintegrating agent selected from the group consisting of carboxymethylcellulose and insoluble reticulated PVP, and at least one swelling agent selected from the group consisting of starch, modified starch and microcrystalline cellulose and a direct compression sugar.

6. The tablet of claim 1, wherein the active substance is in the form of uncoated microgranules and is selected from the group consisting of gastrointestinal sedatives, antacids, analgesics, anti-inflammatory agents, coronary vasodilators, peripheral and brain-vasodilators, anti-infectious agents, antibiotics, antiviral agents, antiparasitic agents, anticancerous drugs, antianxiety agents neuroleptic drugs, agents stimulating the central nervous system anti-depressant drugs antihistaminic agents, antidiarrheal agents, laxatives, nutritional supplements, immunodepressant drugs, cholesterol lowering agents, hormones, enzymes, anti-spasmodic agents, antiangorous agents, drugs acting on the rhythm of the heart, drugs used in the treatment of arterial hypertension, anti-migraine agents, drugs acting on blood coagulability, anti-epileptic agents, myorelaxing agents, drugs used in the treatment of diabetes, drugs used in the treatment of thyroidal dysfunctions, diuretical agents, anorexigenic drugs, anti-asthmatic agents, expectorants, antitussive agents, mucoregulators, decongestants, hypnotics, anti-nausea agents, hematopoietical agents, uricosuric agents, plant extracts and contrast mediums.

* * * * *

UNITED STATES PATENT AND TRADEMARK OFFICE
CERTIFICATE OF CORRECTION

PATENT NO. : 5,464,632

DATED : November 7,1995

INVENTOR(S) : Gerard Cousin et al

It is certified that error appears in the above-indentified patent and that said Letters Patent is hereby corrected as shown below:

Column 7, claim 1, line 61, add "of" after consisting.

Signed and Sealed this

Seventh Day of January, 1997

Attest:

BRUCE LEHMAN

*Attesting Officer*  Commissioner of Patents and Trademarks

US005464632C1

(12) REEXAMINATION CERTIFICATE (4273rd)

United States Patent
Cousin et al.

(10) Number: US 5,464,632 C1
(45) Certificate Issued: Feb. 20, 2001

(54) RAPIDLY DISINTEGRATABLE MULTIPARTICULAR TABLET

(75) Inventors: Gérard Cousin, Gallardon; Etienne Bruna, Chartres; Edouard Gendrot, Vernouillet, all of (FR)

(73) Assignee: Laboratoires Prographarm, Chateaueuf-en-Thymerals (FR)

Reexamination Request:
No. 90/005,207, Dec. 31, 1999

Reexamination Certificate for:
Patent No.: 5,464,632
Issued: Nov. 7, 1995
Appl. No.: 08/346,324
Filed: Nov. 29, 1994

Certificate of Correction issued Dec. 12, 1996.

Related U.S. Application Data

(63) Continuation of application No. 08/035,355, filed on Mar. 22, 1993, now abandoned.

(30) Foreign Application Priority Data

Jul. 22, 1991 (FR) .................................... 91 09245

(51) Int. Cl.[7] ...................................................... A61K 9/20
(52) U.S. Cl. ........................ 424/465; 424/489; 424/490; 424/495; 424/497
(58) Field of Search .................................. 424/465, 489, 424/490, 495, 497

(56) References Cited

U.S. PATENT DOCUMENTS

| | | |
|---|---|---|
| 2,887,437 | 5/1959 | Klioze et al. . |
| 3,488,418 | 1/1970 | Holliday et al. . |
| 3,524,190 | 8/1970 | Holliday et al. . |
| 3,882,228 | 5/1975 | Boncey et al. . |
| 4,016,254 | 4/1977 | Seager . |
| 4,017,598 | 4/1977 | Ohno et al. . |
| 4,371,516 | 2/1983 | Gregory et al. . |
| 4,547,359 | 10/1985 | Zierenberg et al. . |
| 4,574,080 | 3/1986 | Roswall et al. . |
| 4,666,703 | 5/1987 | Kopf . |
| 4,687,662 | 8/1987 | Schobel . |
| 4,710,384 | 12/1987 | Rotman . |
| 4,760,093 | 7/1988 | Blank et al. . |
| 4,832,956 | 5/1989 | Gergley et al. . |
| 4,851,226 | 7/1989 | Julian et al. . |
| 4,867,987 | 9/1989 | Seth . |
| 4,874,614 | 10/1989 | Becker . |
| 4,886,669 | 12/1989 | Ventouras . |
| 4,904,477 | 2/1990 | Ho et al. . |
| 4,915,953 | 4/1990 | Jordan et al. . |
| 4,940,588 | 7/1990 | Sparks et al. . |
| 5,047,247 | 9/1991 | Milovac et al. . |
| 5,073,374 | 12/1991 | McCarty . |
| 5,073,377 | 12/1991 | Alexander et al. . |
| 5,178,878 | 1/1993 | Wehling et al. . |
| 5,198,228 | 3/1993 | Urban et al. . |
| 5,215,756 | 6/1993 | Gole et al. . |
| 5,629,016 | 5/1997 | Fielden et al. . |

FOREIGN PATENT DOCUMENTS

| | | |
|---|---|---|
| 49161/85 | 10/1985 | (AU) . |
| 79507/87 | 10/1987 | (AU) . |
| 33946/89 | 5/1989 | (AU) . |
| 66012/90 | 9/1990 | (AU) . |
| 72560/91 | 2/1991 | (AU) . |
| 003589 A2 | 2/1979 | (EP) . |
| 196546 A2 | 2/1979 | (EP) . |
| 207041 A2 | 6/1986 | (EP) . |
| 250648 A2 | 12/1986 | (EP) . |
| 250648 A3 | 12/1986 | (EP) . |
| 255002 A1 | 7/1987 | (EP) . |
| 266113 | 10/1987 | (EP) . |
| 273005 A1 | 11/1987 | (EP) . |
| 281200 A1 | 2/1988 | (EP) . |
| 313328 A1 | 10/1988 | (EP) . |
| 347767 A1 | 6/1989 | (EP) . |
| 350701 | 6/1989 | (EP) . |
| 408273 A1 | 7/1990 | (EP) . |
| 1134097 | 1/1968 | (GB) . |
| 1548022 | 7/1979 | (GB) . |
| 2067900 | 1/1980 | (GB) . |
| 2086725 | 11/1980 | (GB) . |
| 2087235 | 11/1980 | (GB) . |
| 2086725 | 8/1985 | (GB) . |
| WO91/04757 | 4/1991 | (WO) . |
| WO91/16043 | 10/1991 | (WO) . |

OTHER PUBLICATIONS

Lehman, K., "Formulation of Controlled Release Tablets with Acrylic Resins" Acta. Pharma. Fenn. 93, pp. 55–74 (1984).

Lehman, K.O.R., "Chemistry & Application Properties of Polymethacrylate Coating Systems" in Aqueous Polymeric Coatings for Pharmaceutical Dosage Forms (J.W. McGinity, ed.) pp. 222–234, Marcel Dekker Inc., New York (1989).

Butterworth's Medical Dictionary, 2nd Edition (1978) Butterworths, London, ISBN 0 407 00193 X; p. 1449.

Remington's Pharmaceutical Sciences, 18th Edition (1990) "Disintegrants", Mack Publishing Co, ISBN 0–912734–04–3, p. 1637.

Remington's Pharmaceutical Sciences, Mack Publishing Co. pp. 1604–1605 (1975).

Pharmaceutical Dosage Forms, vol. 1, ed. Lieberman & Lachman, Marcel Decker, Inc., ISBN 0–8247–6918–X (1980), pp. 72–88, 135–136, 289–294.

J. Putter, Med. Welt, Bd. 27/Heft 28, pp. 1362–1365 (1976) (and English Translation).

Rote Liste 1982, 78 002 (and English Translation).

Beipackzettel Colfarit, Sep. 1987 (and English Translation).

(List continued on next page.)

*Primary Examiner*—Thurman K. Page

(57) ABSTRACT

Rapidly disintegratable multiparticulate tablet the excipient mixture of which is suitable for imparting a disintegration rate such that the tablet disintegrates in the mouth in an extremely short time, notably in less than sixty seconds, characterized by the fact that the active substance is present in the form of coated microcrystals or coated or uncoated microgranules.

OTHER PUBLICATIONS

Auszug aus der Herstellungvorschrift fur Colfarit, gutig ab Jun. 19, 1990 with the abstract Apr. 3, 1991 gutigen Zerfallstest (and English Translation).

"Tablettieren" "verpressen von uberzognen Partikein zu zerfallenden Tabletten mit knotrollerter Wirkstoffabgabe" of May 9–May 11, 1990 (and English Translation).

Duchene, D. "Tablet disintegration" in Topics in Pharmaceutical Sciences, (1983), (D.D. Bremer and P. Speiser, eds) p. 387–399, Elsevier Science Publishers, Amsterdam, New York and Oxford (and English Translation).

The Theory & Practice of Industrial Pharmacy, Lea & Febiger, pp. 320–321,, 325–328, 412–429 (1986).

Merck Index, pp. 6, 114, 156, 247, 248, 649 1109 (1976).

Saki, A, and Oyola, J.R. (1986) "Some Factors Affecting the Dissolution of Microencapsulated Potassium Chloride in Directly Compressed Tablets"Pharm, Ind. 48, 92–94 (Saki).

Seager, H. (1977), "Spray–Coating Bulk Drugs aids Dosage Form Production", Manufacturing Chemist and Aerosol News, Apr. 1977, 25–35 (Seager).

Lang, S., (1982), "Developments in Tablet Disintegrants", Manufacturing Chemist, Mar. 1982, pp. 31–33 (Lang).

Wan, L.S.C. and Prasad, K.P.P. (1988), "Effect of Microcrystalline Cellulose and Cross–Linked Sodium Carboxymethylcellulose on the Properties of Tablets with Methyl Cellulose as a Binder", International Journal of Pharmaceutics, 41, 159–167 (Wan).

US 5,464,632 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 6 is cancelled.

Claims 1 and 4 are determined to be patentable as amended.

Claims 2, 3, 5, dependent on an amended claim, are determined to be patentable.

1. A rapidly disintegratable tablet for oral administration [with or] *and disintegration in the buccal cavity* without the use of water, *wherein* said tablet [comprising] *comprises* an active substance and a mixture of *non-effervescent* excipients [wherein said active substance is] *and permits to obtain reduced ph influence in the digestive tract and reduced influence of viscosity, said active substance being* multiparticulate and in the form of coated microcrystals, *or* coated microgranules [or uncoated microgranules] and wherein said mixture of excipients comprises [excipients which are responsible for the disintegration, said tablet being intended to be swallowed said disintegration occurring in less than sixty seconds under the action of the excipients which are responsible for the disintegration and which are selected from the group consisting at least one ] *a* disintegrating agent and [at least one] swelling agent *which are responsible for the disintegration of the tablet with the saliva present in the mouth, to achieve in less than 60 seconds a suspension easy to swallow.*

4. The tablet of claim 1, wherein the mixture of excipients comprises at least one disintegrating agent selected from the group consisting of carboxymethylcellulose, insoluble reticulated PVP [type] and at [lest] *least* one swelling agent selected from the group consisting of starch, modified starch and microcrystalline cellulose.

* * * * *